United States Patent [19]

Bjorge et al.

[11] Patent Number: 5,385,929

[45] Date of Patent: Jan. 31, 1995

[54] [(HYDROXYPHENYLAMINO) CARBONYL] PYRROLES

[75] Inventors: Susan M. Bjorge, Ann Arbor; Ann E. Black, Tecumseh; Bruce D. Roth, Ann Arbor; Thomas Woolf, Dexter, all of Mich.

[73] Assignee: Warner-Lambert Company, Morris Plains, N.J.

[21] Appl. No.: 238,120

[22] Filed: May 4, 1994

[51] Int. Cl.$^6$ ................ A61K 31/40; C07D 405/06; C07D 207/327

[52] U.S. Cl. .................... 514/422; 514/423; 548/517; 548/537; 548/406

[58] Field of Search ............... 548/517, 537; 514/422, 514/423

[56] References Cited

U.S. PATENT DOCUMENTS

| | | | |
|---|---|---|---|
| 4,681,893 | 7/1987 | Roth | 514/422 |
| 5,216,174 | 6/1993 | Butler et al. | 548/517 |
| 5,245,047 | 9/1993 | Butler et al. | 548/537 X |
| 5,273,995 | 12/1993 | Roth | 514/422 |
| 5,280,126 | 1/1994 | Butler et al. | 548/517 |
| 5,298,627 | 3/1994 | Butler et al. | 548/517 |

OTHER PUBLICATIONS

Pharmaceutical Research (PHReeB) 10(10) S1–S454 (1993) ISSN 0724–8741 "Development and Validation of an Enzyme Inhibition Assay for Quantitation of Cl-981 in Human Plasma" Y. Y. Shum et al.

Primary Examiner—Joseph Paul Brust
Attorney, Agent, or Firm—Charles W. Ashbrook

[57] ABSTRACT

2-(4-Fluorophenyl)-$\beta$,$\delta$-dihydroxy-5-(1-methylethyl)-3-phenyl-4-[(hydroxyphenylamino)carbonyl]-1H-pyrrole-1-heptanoic acid, and their lactone forms, and salts and solvates thereof, inhibit cholesterol biosynthesis, and thus are useful in treating hypercholesterolemia.

18 Claims, No Drawings

[(HYDROXYPHENYLAMINO) CARBONYL] PYRROLES

BACKGROUND OF THE INVENTION

The present invention relates to certain hydroxylated derivatives of compounds known to be useful as inhibitors of cholesterol biosynthesis.

U.S. Pat. No. 4,681,893, which is incorporated herein by reference, discloses compounds which include trans (±)-5-(4-fluorophenyl)-2-(1-methylethyl)-N, 4-diphenyl-1-[2-(tetrahydro-4-hydroxy-6-oxo-2H-pyran-2-yl)ethyl]-1H-pyrrole-3-carboxamides, and the corresponding ring-opened acids derived therefrom, and pharmaceutically acceptable salts thereof. One compound from within the group has been found particularly active in inhibiting the biosynthesis of cholesterol, and is thus especially useful in treating atherosclerosis. Specifically, U.S. Pat. No. 5,273,995, which is incorporated herein by reference, describes the optically pure compound, [R-(R*,R*)]-2-(4-fluorophenyl)-$\beta$,$\delta$-dihydroxy-5-(1-methylethyl)-3-phenyl-4-[(phenylamino)carbonyl]-1H-pyrrole-1-heptanoic acid, pharmaceutically acceptable salts thereof, and the corresponding cyclized lactone form, as being particularly active as a hypocholesterolemic agent. We have now discovered that these compounds are metabolized in vivo to certain phenyl hydroxy derivatives, and that such phenyl hydroxy derivatives are also active as inhibitors of the biosynthesis of cholesterol, and thus can be administered directly to mammals for treating conditions of hypercholesterolemia. An object of this invention therefore is to provide new chemical entities, formulations containing the same, and a method for treating subjects suffering from hypercholesterolemia by administering directly a [(hydroxyphenylamino)carbonyl]pyrrole.

SUMMARY OF THE INVENTION

The present invention provides hydroxyphenyl compounds of Formula I

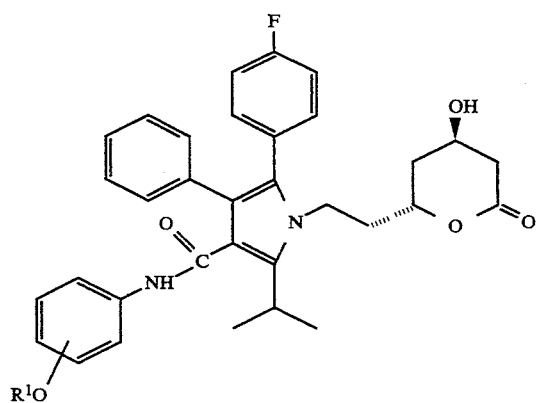

and the open chain acid form of Formula II

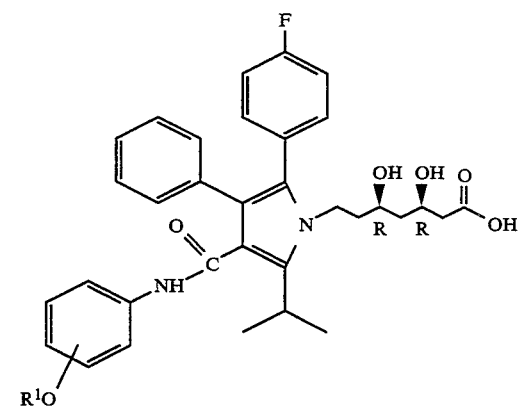

where $R^1$ is hydrogen or a hydroxy protecting group, and the pharmaceutically acceptable salts and solvates thereof. The salts and solvates are prepared as described in U.S. Pat. No. 4,681,893. The invention additionally provides pharmaceutical formulations comprising the lactone of Formula I, or the heptanoic acid form of Formula II, and its pharmaceutically acceptable salts and solvates, together with a pharmaceutically acceptable carrier. Further, the invention provides a method of treating mammals suffering from conditions of hypercholesterolemia by administering a pharmaceutical formulation of the invention.

The compounds of the invention can be prepared by any of several alternative methods. For example, a suitably substituted N-acyl-N-alkyl amino acid can be reacted with a substituted hydroxyphenyl acetylenic compound in accordance with the general process described in U.S. Pat. No. 4,681,893 to give a pyrrole which bears a hydroxyphenyl (or protected hydroxyphenyl) substituent. The reaction is depicted by the following scheme

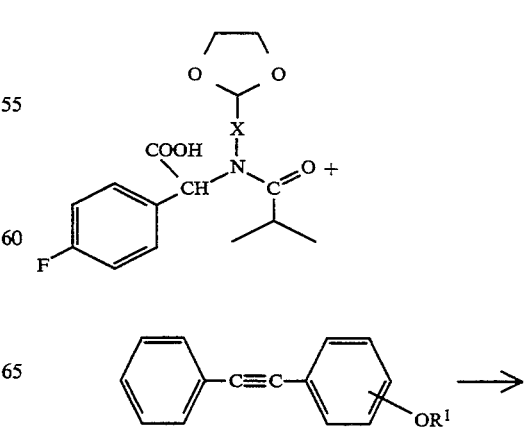

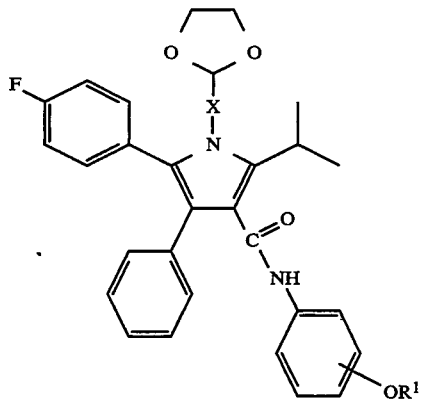

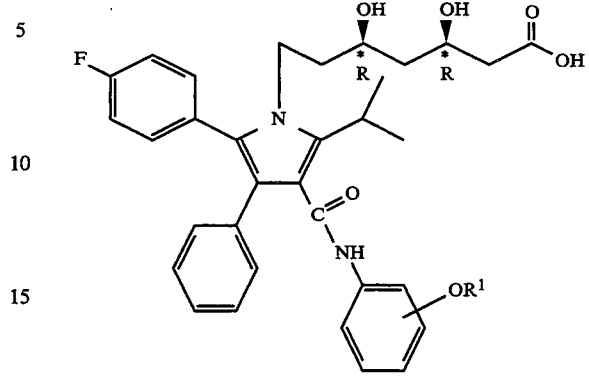

where R[1] is hydrogen, or preferably a hydroxy protecting group which can be easily removed when desired by conventional methods, for example, a benzyl group, and X is a lower alkylene group such as methylene or ethylene. Hydrolysis of the acetal according to the method of U.S. Pat. No. 4,681,893 provides an aldehyde of the formula

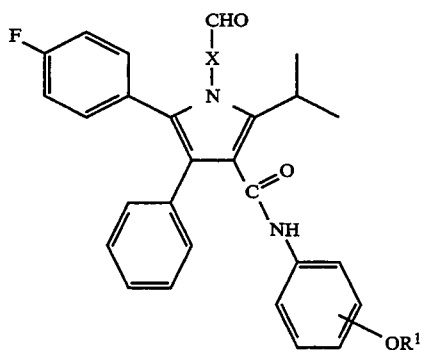

which is reacted with a dilithium or lithio-sodio salt of methyl acetoacetate to produce the corresponding 7-pyrrolo-5-hydroxy-3-oxoheptanoate, which then is reduced with sodium borohydride, for example to a compound of the formula Removal of the hydroxy protecting group R[1] by conventional means provides the hydroxyphenyl pyrroles of the invention, i.e., where R[1] is hydrogen.

The term "hydroxy protecting group" carries its conventional meaning of any organic radical that can be bonded to oxygen to prevent unwanted reactions at that site, yet can be easily removed when desired to generate a hydroxy group.

Typical hydroxy protecting groups include acyl moieties such as acetyl, chloroacetyl, and dichloroacetyl; as well as ether forming groups such as benzyl, trimethylsilyl, and the like. Such readily removable hydroxy protecting groups are more fully described by H. Haslam in *Protective Groups in Organic Chemistry*, McOmie, J. F. W., Ed., Plenum Press, New York, N.Y., 1973, Chapter 3.

An alternative and preferred method for preparing the invention compounds follows the procedure described in U.S. Pat. No. 5,216,174, which is incorporated herein by reference.

Specifically, a 1-protected hydroxyphenylamino-2-isopropylcarbonyl-3-phenyl-4-(4-fluorophenyl)-1,4-dioxobutane (e.g., R[1] is benzyl, acetyl, or the like) is reacted with an optically active R,R-6-(2-aminoethyl)-2,2-dimethyl-1,3-dioxane4-acetic acid according to the scheme

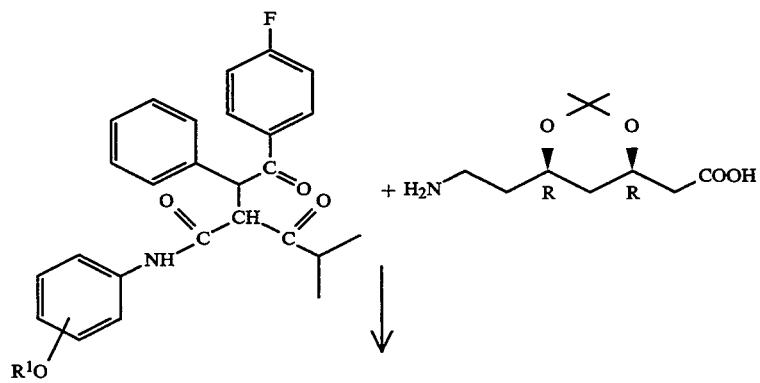

-continued

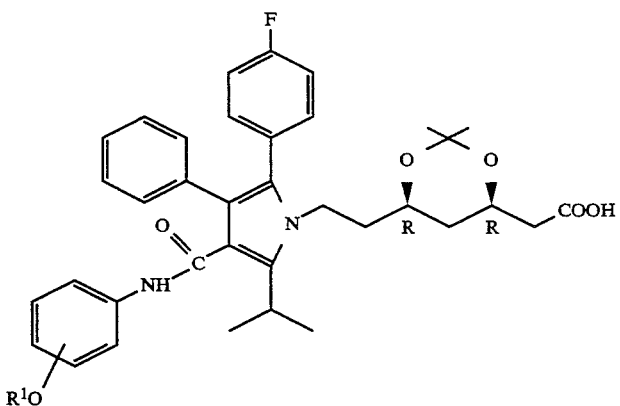

The foregoing intermediate generally is not isolated, but rather is reacted directly with an acid such as hydrochloric acid to provide a lactone of the formula

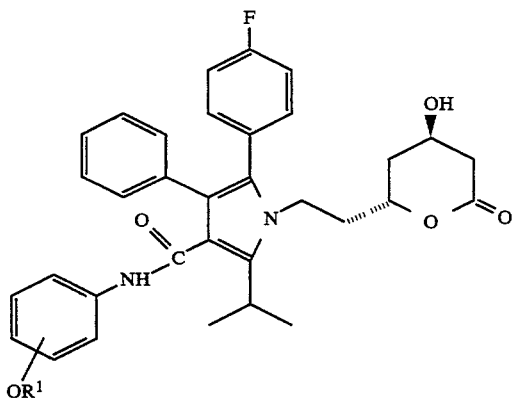

The R¹ protecting group is removed by conventional procedures, for instance, hydrogenation over a catalyst such as palladium in the case where R¹ is benzyl, to provide an invention compound in the form of the lactone, which can readily be converted to the ring-opened dihydroxy heptanoic acid by simple aqueous hydrolysis. The heptanoic acids are readily converted to pharmaceutically acceptable acid addition salts by reaction with a base such as sodium hydroxide or methylamine.

The [(hydroxyphenylamino)carbonyl]pyrroles of this invention can be formulated with conventional carriers and excipients, and administered to animals for inhibiting the biosynthesis of cholesterol, all according to the teachings of U.S. Pat. Nos. 4,681,893 and 5,273,995.

The preparation of the hydroxyphenyl compounds of this invention is more fully described by the following detailed examples, which are illustrative only and are not to be construed as limiting the invention in any way.

EXAMPLE 1

[3R,5R]-2-Fluorophenyl-$\beta,\delta$-dihydroxy-5-(1-methylethyl)-3-phenyl-4-[(4-hydroxyphenylamino)carbonyl]-1H-pyrrole-1-heptanoic acid, sodium salt A. Preparation of 4-methyl-3-oxo-N-(4-benzyloxophenyl)-2-(phenylmethylene) pentamide of the formula

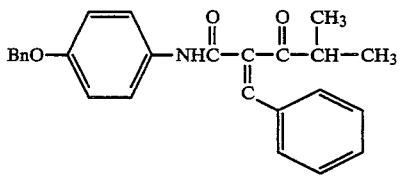

A mixture of 14 g (97 mmol) of methyl isobutyryl acetate, 11.6 g (97.3 mmol) of 4-benzyloxyaniline, and 0.07 mL (1 mmol) of 1,2-ethylene diamine in 500 mL of xylenes was stirred and heated at reflux for 16 hours. Water was removed via a Dean-Stark trap. The solution was cooled to 30° C. and stirred while 10 mL (100 mmol) of benzaldehyde and 0.5 mL of pyridine were added. The mixture was again heated to reflux and stirred for 2 hours, after which it was cooled to 24° C. and concentrated to an oil by evaporation of the solvent under reduced pressure. The oil was purified by chromatography over silica gel, eluting with hexane-ethyl acetate (20:1 v/v). Fractions containing the major component (by tlc) were combined, and the solvent was removed by evaporation under reduced pressure to give 9.0 g of an oil. The oil was crystallized from isopropanol to provide 9.0 g of 4-methyl-3-oxo-N-(4-benzyloxyphenyl)-2-(phenylmethylene)pentamide.

Analysis calculated for $C_{26}H_{25}NO_3$. Theory: C, 78.17; H, 6.31; N, 3.57. Found: C, 78.34; H, 6.11; N, 3.57. IR: 1686, 1675, 1669, 1662, 1652, 1644, 1640, 1597 cm$^{-1}$. 200 MHz NMR (CDCl$_3$): $\delta$ 1.02 (d, 6H, J=7 Hz), 2.61 (septet, 1H, J=7 Hz), 5.05 (s, 2H), 6.9–7.6 (m, 14H), 8.15 (s, 1H), 8.92 (bs, 1H).

B. Preparation of 4-methyl-3-oxo-N-(4-benzyloxyphenyl)-2-[1-phenyl-2-(4-fluorophenyl)-2-oxoethyl]pentamide of the formula

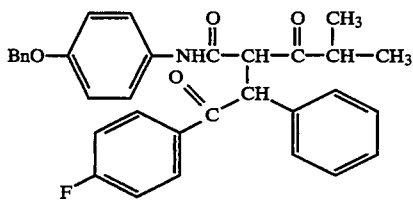

Two and one-half grams (10 mmol) of 3-ethyl-5-(2-hydroxyethyl)-4-methylthiazolium bromide was dissolved in 50 mL of ethanol and the solution was concentrated to dryness by evaporation under reduced pressure. This was repeated three times to give an oil. The oil was then dissolved in 350 mL of ethanol, to which were added 19.3 g (48.3 mmol) of 4-methyl-3-oxo-N-(4-benzyloxyphenyl)-2-(phenylmethylene)pentamide (prepared as described in A above) 5.5 mL (51 mmol) of 4-fluorobenzaldehyde, and 4.9 mL (35 mmol) of triethylamine. The mixture was heated to 110° C., and an additional 2 mL of triethylamine were added. The solution was stirred at 90° C. for 12 hours, cooled to 24° C., and diluted with 100 mL of ethylacetate. The mixture was washed with water, with dilute 6N HCl, with brine solution, and dried over magnesium sulfate. The mixture was filtered and the solvent was removed from the filtrate by evaporation under reduced pressure to give 14 g of an oil. The oil was combined with 13 g of an oil obtained by repeating the above procedure. The combined oil was purified by chromatography over silica gel, eluting with a gradient solvent mixture of hexane and ethyl acetate (10:1–2:1 v/v). Fractions shown by tlc to contain the major component were combined and the solvent was removed by evaporation to afford 23 g of 4-methyl-3-oxo-N-(4-benzyloxyphenyl)-2-[1-phenyl-2-(4-fluorophenyl)-2-oxoethyl]pentamide.

Analysis calculated for $C_{33}H_{30}FNO_4$ Theory: C, 75.70; H, 5.78, N, 2.68. Found: C, 75.76; H, 5.89; N, 2.87.

C. Preparation of (4R-cis)-1,1-dimethylethyl-6-[2-[2-(4-fluorophenyl)-5-(1-methylethyl)-3-phenyl-4-[(4-benzyloxyphenyl)carbonyl]-1H-pyrrol-1-yl]-ethyl]-2,2-dimethyl-1,3-dioxane-4-acetate of the formula

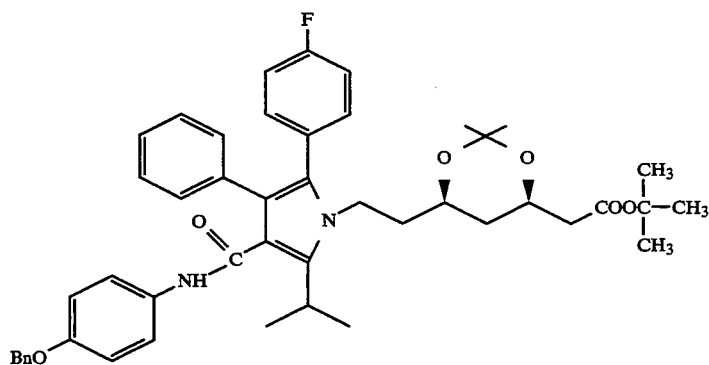

A mixture of 8.9 g (17 mmol) of 4-methyl-3-oxo-N-(4-benzyloxyphenyl)-2-[1-phenyl-2-(4-fluorophenyl)-2-oxoethyl]pentamide (from Step B above) and 4.8 g (17.5 mmol) of (4R-cis)-1,1-dimethylethyl-6-(2-aminoethyl)-2,2-dimethyl-1,3-dioxane-4-acetate (prepared as described in U.S. Pat. No. 5,216,174 and EPO 330172A2, incorporated herein by reference) in 90 mL of 4:1:1 (v/v/v/) heptane-toluene-tetrahydrofuran containing 1.8 g (17.5 mmol) of pivalic acid, was heated at reflux for 48 hours. The solution was cooled to 24° C., diluted with 100 mL of ethyl acetate, washed with water, 6N HCl, saturated aqueous sodium bicarbonate, and brine, and dried over magnesium sulfate. The mixture was filtered and the filtrate was concentrated to dryness by evaporation under reduced pressure to provide the title compound in 90% yield.

D. Preparation of (2R-trans)-5-(4-fluorophenyl)-2-(1-methylethyl)-N-(4-benzyloxyphenyl)-4-phenyl-1-[2-(tetrahydro-4-hydroxy-6-oxo-2H-pyran-2-yl)ethyl]-1H-pyrrole-3-carboxamide of the formula

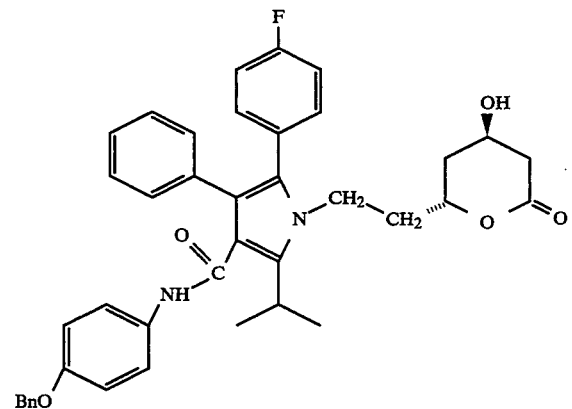

A solution of 134 g (17 mmol) of (4R-cis)-1,1-dimethylethyl-6-[2-[2-(4-fluorophenyl)5-(1-methylethyl)-3-phenyl-4-[(4-benzyloxyphenyl)carbonyl]-1H-pyrrol-1-yl]ethyl]-2,2-dimethyl-1,3-dioxane-4-acetate (prepared according to C above) in 240 mL of a mixture of 1N hydrochloric acid: methanol:tetrahydrofuran (2:5:5: v/v/v) was stirred at 24° C. for 12 hours. Forty grams (100 mmol) of sodium hydroxide were added and the solution was stirred 5 hours at 24° C. The mixture was concentrated to about 50 mL by evaporation of solvents under reduced pressure, and the solution was added to 500 mL of diethyl ether and 1000 mL of water. The aqueous layer was separated and acidified to pH 1 by addition of 1N hydrochloric acid. The acidic solution was extracted two times with 500-mL portions of ethyl acetate. The extracts were combined, washed with water, dried over magnesium sulfate, and concentrated to dryness by evaporation under reduced pressure. The solid which remained was dissolved in 100 mL of toluene and heated at reflux for 4 hours in a flask equipped with a Dean-Stark trap. The solution was cooled to 24° C. and concentrated to an oil by evaporation under reduced pressure. The oil was purified by chromatography over silica gel (eluting with ethyl acetate) to provide, after removal of the solvent, 4.87 g of the title compound.

Analysis calculated for $C_{40}H_{39}FN_2O_5$ Theory: C, 74.28; H, 6.08; N, 4.33. Found: C, 73.49; H, 6.24; N, 3.95. IR (KBr): 3400, 1734, 1684, 1647, 1509, 1230 cm$^{-1}$. 250 MHz H$^1$ NMR (CDCl$_3$): δ 1.5 (m, 6H), 1.6–2.0 (m, 4H), 2.40 (br s, 1H), 2.45 (m, 1H), 2.63 (dd, 1H, J=5.4, 17.8 Hz), 3.5 (septet, 1H, J=7 Hz), 3.9–4.3 (m, 3H), 4.52 (m, 1H), 4.90 (s, 2H), 6.80 (d, 2H, J=9.0 Hz), 6.9–7.4 (m, 17H). CI MS M+ 647.

E. Synthesis of (2R-trans)-5-(4-fluorophenyl)-2-(1-methylethyl)-N-(4-hydroxyphenyl)-4-phenyl-1-[2-(tetrahydro-4-hydroxy-6-oxo-2H-pyran-2-yl)-ethyl]-1H-pyrrole-3-carboxamide of the formula

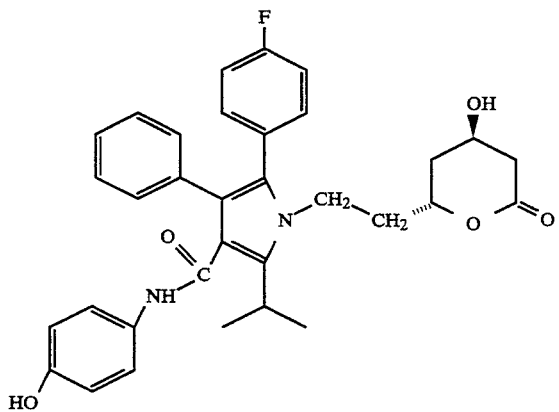

A mixture of 4.7 g (7.26 mmol) of the benzyl ether from Step D above and 1.0 g of 10% palladium on carbon in 300 mL of ethyl acetate was stirred at 24° C. under hydrogen for 3 days. The mixture was filtered to remove the catalyst, and the solvent was removed by evaporation under reduced pressure to give an oil. The oil was crystallized from fresh ethyl acetate to provide 3.5 g of (2R-trans)-5-(4-fluorophenyl)-2-(1-methylethyl)-N-(4-hydroxyphenyl)-4-phenyl-1-[2-(tetrahydro-4-hydroxy-6-oxo-2H-pyran-2-yl)-ethyl]-1H-pyrrole-3-carboxamide (containing 0.5 mol of ethyl acetate), mp 130°–133° C.

Analysis calculated for $C_{33}H_{33}FN_2O_5$ Theory: C, 71.21; H, 5.98; N, 5.03. Found: C, 69.78; H, 6.17; N, 4.70. FAB MS 557.4 250 MHz H$^1$ NMR (CDCl$_3$): δ 1.51 (m, 6H), 1.5–2 (m, 4H), 2.57 (d, 2H, J=4.0 Hz), 3.45 (septet, 1H, J=7 Hz), 3.9–4.2 (m, 3H), 4.55 (m, 1H), 6.67 (d, 2H, J=9 Hz ), 6.96 (d, 2H, J=9 Hz ), 7.0–7.3 (m, 9H). IR (KBr): 3400, 3296, 1720, 1684, 1540, 1247 cm$^{-1}$.

F. Synthesis of [3R,5R]-2-fluorophenyl-β,δ-dihydroxy-5-(1-methylethyl)-3-phenyl-4-[(4-hydroxyphenylamino)carbonyl]-1H-pyrrole-1-heptanoic acid, sodium salt.

To a stirred solution of 0.9 g (1.62 mmol) of the lactone from Step E above in 20 mL of tetrahydrofuran was added a solution of 0.062 mg (1.62 mmol) of sodium hydroxide in 10 mL of water. The solution was stirred at 24° C. for 12 hours. The mixture was concentrated by evaporation of the solvent under reduced pressure to give an aqueous oil. The oil was dissolved in 50 mL of toluene:methanol (9:1 v/v), and the solution was again concentrated by removal of solvents under reduced pressure. This latter step was repeated three times, after which the final removal of solvents provided 900 mg of a solid identified as [3R,5R]-2-(4-fluorophenyl)-β,δ-dihydroxy-5-(1-methylethyl)-3-phenyl-4-[(4-hydroxyphenylamino)carbonyl]-1H-pyrrole-1-heptanoic acid, sodium salt.

Analysis calculated for $C_{33}H_{34}FN_2O_6Na$ Theory: C, 66.43; H, 5.74; N, 4.70. Found: C, 65.81; H, 6.27; N, 3.93. FAB MS: 597.619 +Q3 MS: 596.3 250 MHz H$^1$ NMR (DMSO-d$_6$): δ 1.36 (d, 6H, J=7 Hz), 1.4–1.6 (m, 4H), 1.82 (dd, 1H, J=8, 15 Hz), 2.03 (dd, 1H, J=4, 15 Hz), 3.20 (septet, 1H, J=7 Hz), 3.5 (m, 1H), 3.65 (m, 1H), 3.7–4.1 (m, 2H), 6.58 (d, 1H, J=9 Hz), 7.0–7.3 (m, 11H), 8.33 (s, 1H), 9.52 (s, 1H).

EXAMPLE 2

Following the general procedure set forth in Example 1, 4-methyl-3-oxo-N-(3-benzyloxyphenyl)-2-(phenylmethylene)pentamide of the formula

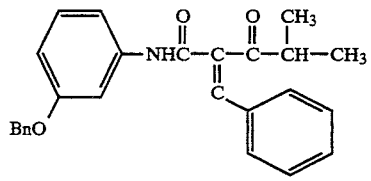

was prepared utilizing 3-benzyloxyaniline and converted (as in Steps B–F above) to the lactone (2R-trans)-5-(4-fluorophenyl)-2-(1-methylethyl)-N-(3-hydroxyphenyl)-4-phenyl-1-[2-(tetrahydro-4-hydroxy-6-oxo-2H-pyran-2-yl)ethyl]-1H-pyrrole3-carboxamide of the formula

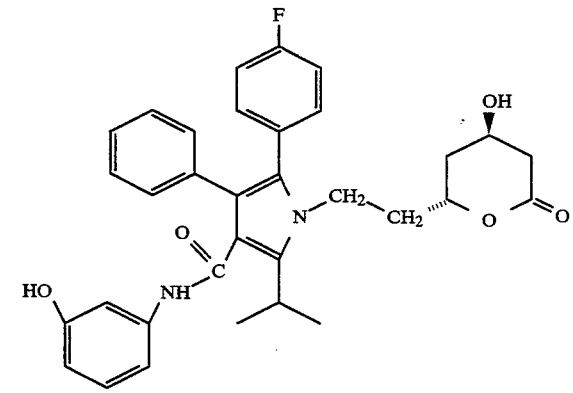

mp 103°–105° C.

The product was shown to contain 0.5 mole of ethyl acetate as a solvent.

IR (KBr): 3402, 2964, 1714, 1652, 1602, 1532, 1256, and 1225 cm$^{-1}$; 250 MHz H$^1$ NMR (CDCl$_3$): δ 1.5 (m, 6H), 1.6–2.0 (m, 4H), 2.6 (m, 2H), 3.54 (septet, 1H, J=7 Hz), 4.0–4.3 (m, 3H), 4.51 (m, 1H), 6.0 (d, 1H, J=8 Hz), 6.51 (dd, 1H, J=2.8 Hz), 6.9–7.6 (m, 11H).

The lactone (0.92 g, 1.65 mmol) was reacted with aqueous sodium hydroxide (1.65 mL of 1 M) to provide 640 mg (65% yield) of [3R,5R]-2-fluorophenyl-β,δ-dihydroxy-5-1-methylethyl-3-phenyl-4-[(3-hydroxyphenylamine)carboxyl]-1H-pyrrole-1-heptanoic acid, sodium salt as an amorphous powder;

Analysis calculated for $C_{33}H_{34}FN_2O_6Na \cdot 2H_2O$ Theory: C, 62.55; H, 6.20; N, 4.42. Found: C, 62.25; H, 6.02; N, 4.08.

EXAMPLE 3

By following the general procedure of Example 1, 2-benzyloxyaniline was reacted with methyl isobutyryl acetate and 1,2-ethylene diamine to provide 4-methyl-3-oxo-N-(2-benzyloxyphenyl)-2-(phenylmethylene)pentamide of the formula

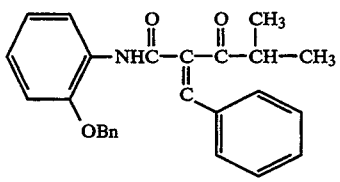

This was converted, by the general procedures of Steps B–F, to the lactone (2R-trans)-5-(4-fluorophenyl)-2-(1-methylethyl)-N-(2-hydroxyphenyl)-4-phenyl-1-[2-(tetrahydro-4-hydroxy-6-oxo-2H-pyran-2-yl)ethyl]-1H-pyrrole-3-carboxamide of the formula

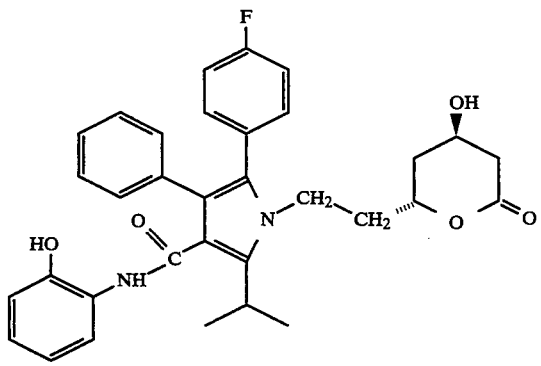

mp 113°–114° C.; IR (KBr): 3408, 2926, 1734, 1716, 1635, 1508 cm$^{-1}$. 400 MHz H$^1$ NMR (CDCl$_3$): δ 1.54 (m, 6H), 1.6–2.0 (m, 4H), 2.6 (d, 1H, J=12 Hz), 2.68 (dd, 1H, J=5, 12 Hz ), 3.64 ( septet, 1H, J=7 Hz ), 4.05 (m, 1H), 4.25 (m, 1H), 4.35 (m, 1H), 4.56 (m, 1H), 5.66 (d, 1H, J=10 Hz) 6.60 (t, 1H, J=10 Hz), 6.9–7.3 (m, 13H).

The lactone was reacted with sodium hydroxide in water to give [3R,5R]-2-fluorophenyl-β,δ-dihydroxy-5-(1-methylethyl)-3-phenyl-4-[(2-hydroxyphenylamino)-carbonyl]-1H-pyrrole-1-heptanoic acid, sodium salt, mp 175°–180° C. (dec).

As pointed out above, the compounds of the invention have shown excellent activity in inhibiting cholesterol biosynthesis by inhibiting the HMG-CoA reductase enzyme. The compounds were evaluated in a standard in vitro assay designed to measure percent inhibition of HMG-CoA reductase at various concentrations in human plasma.

The assay is described more fully by Shum, et al., in *Pharmaceutical Research*, 10(10):S1–S454 (1993), PPDM 8467, which is incorporated herein by reference for its teaching of the assay methodology. The table below reports the percent of inhibition of the compounds of this invention at various concentration levels, as well as the activity for the compound described in U.S. Pat. No. 5,273,995, which is a precursor to the hydroxyphenyl derivatives of this invention.

TABLE I

| Percent Inhibition of HMG-CoA Reductase in Blood Plasma | | |
|---|---|---|
| Compound | 10 ng/mL | 1 ng/mL |
| Compound of Patent 5,273,995 (open form) | 100 | 100 |
| Compound of Patent 5,273,995 (lactone) | 76 | 98 |
| Compound of Example 1E (lactone) | 100 | 87 |
| Compound of Example 1F (open form) | 100 | 100 |
| Compound of Example 2 (lactone) | 51 | 49 |
| Compound of Example 2 (open form) | 90 | 80 |
| Compound of Example 3 (open form) | 57 | 51 |

We claim:

1. A compound of the formula

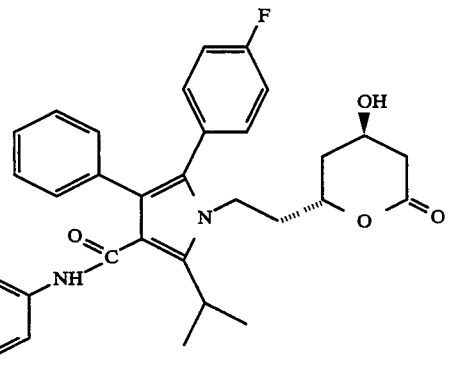

where R$^1$ is hydrogen or a hydroxy protecting group and solyates thereof or the open chain form of the formula

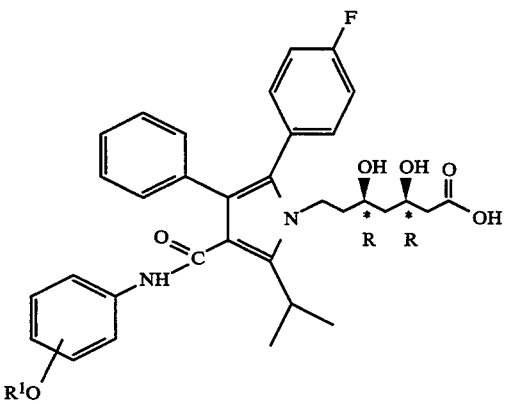

and the pharmaceutically acceptable salts and solyates thereof.

2. A compound of claim 1 wherein R$^1$ is benzyl.

3. A compound of claim 1 wherein R$^1$ is hydrogen.

4. A compound of claim 3 which is

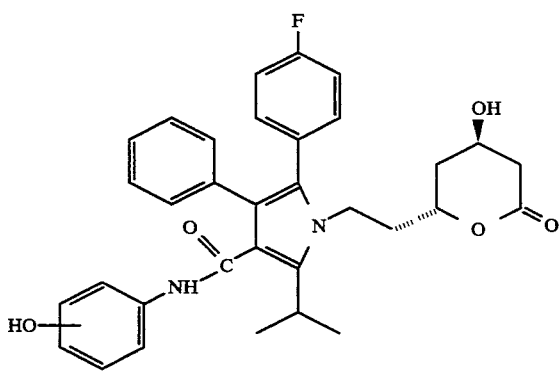

5. The compound of claim 4 which is (2R-trans)-5-(4-fluorophenyl)-2-(1-methylethyl)-N-(4-hydroxyphenyl)-4-phenyl-1-[2-(tetrahydro-4-hydroxy-6-oxo-2H-pyran-2-yl)ethyl]-1H-pyrrole-3-carboxamide.

6. The compound of claim 4 which is (2R-trans)-5-(4-fluorophenyl)-2-(1-methylethyl)-N-(3-hydroxyphenyl)-4-phenyl-1-[2-(tetrahydro-4-hydroxy-6-oxo-2H-pyran-2-yl)ethyl]-1H-pyrrole-3-carboxamide.

7. The compound of claim 4 which is (2R-trans)-5-(4-fluorophenyl)-2-(1-methylethyl)-N-(2-hydroxyphenyl)-4-phenyl-1-[2-(tetrahydro-4-hydroxy-6-oxo-2H-pyran-2-yl)ethyl]-1H-pyrrole-3-carboxamide.

8. A compound of claim 3 which is

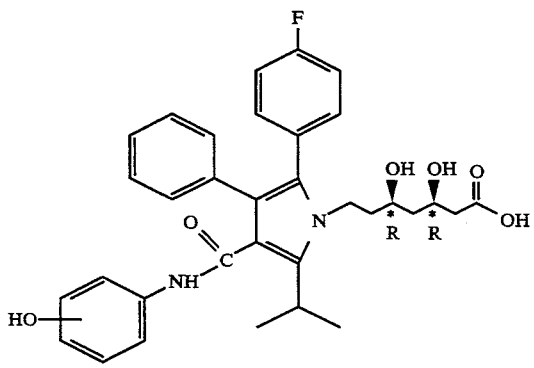

or a pharmaceutically acceptable salt thereof.

9. The compound of claim 8 which is [3R,5R]-2-(4-fluorophenyl)-β,δ-dihydroxy-5-(1-methylethyl)-3-phenyl-4-[(4-hydroxyphenylamino)carbonyl]-1H-pyrrole-1-heptanoic acid, sodium salt.

10. The compound of claim 8 which is [3R,5R]-2-fluorophenyl-β,δ-dihydroxy-5-1-methylethyl- 3-phenyl-4-[(3-hydroxyphenylamine)carboxyl]-1H-pyrrole-1-heptanoic acid, sodium salt.

11. The compound of claim 8 which is [3R,5R]-2-fluorophenyl-β,δ-dihydroxy-5-(1-methylethyl)-3-phenyl-4-[(2-hydroxyphenylamino)carbonyl]-1H-pyrrole-1-heptanoic acid, sodium salt.

12. A pharmaceutical formulation comprising a compound of claim 1 together with a pharmaceutically acceptable carrier.

13. A formulation of claim 12 wherein the active ingredient is a compound in which $R^1$ is hydrogen.

14. A formulation of claim 13 wherein the active ingredient is a compound of the formula

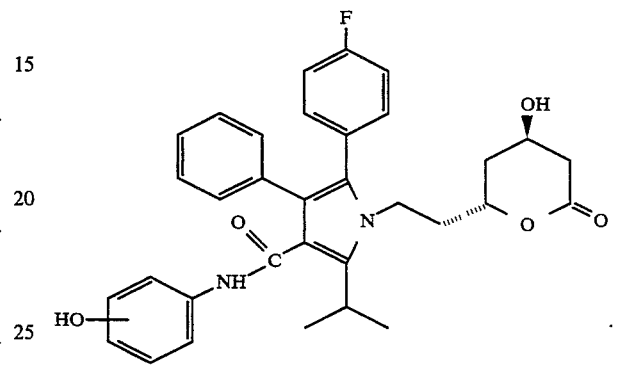

15. A formulation of claim 13 wherein the active ingredient is a compound of the formula

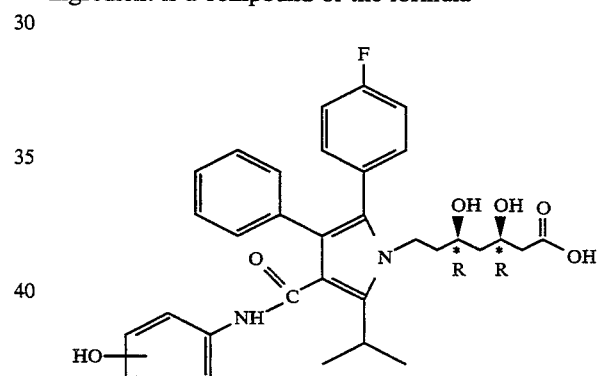

or a pharmaceutically acceptable salt thereof.

16. A method of inhibiting cholesterol synthesis in an animal comprising administering a compound of claim 1.

17. The method of claim 16 employing a compound wherein $R^1$ is hydrogen.

18. A method of treating a mammal suffering from conditions of hypercholesterolemia by administering a compound of claim 1 wherein $R^1$ is hydrogen.

* * * * *